(12) United States Patent
Paliard

(10) Patent No.: US 6,919,318 B1
(45) Date of Patent: Jul. 19, 2005

(54) ENHANCING IMMUNE RESPONSES TO GENETIC IMMUNIZATION BY USING A CHEMOKINE

(75) Inventor: Xavier Paliard, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/673,798

(22) PCT Filed: Apr. 22, 1999

(86) PCT No.: PCT/US99/08802

§ 371 (c)(1),
(2), (4) Date: Oct. 19, 2000

(87) PCT Pub. No.: WO99/53960

PCT Pub. Date: Oct. 28, 1999

Related U.S. Application Data
(60) Provisional application No. PCT/US99/08802, filed on Apr. 22, 1999.

(51) Int. Cl.[7] .................. A61K 48/00; A61K 38/00; A61K 38/43; C12N 15/74; C07K 14/00
(52) U.S. Cl. ................. 514/44; 514/2; 435/320.1; 424/184.1; 424/188.1; 424/189.1; 530/350
(58) Field of Search .............. 514/44, 2; 435/320.1; 424/188.1, 189.1, 184.1; 530/350

(56) References Cited

U.S. PATENT DOCUMENTS

| | | | |
|---|---|---|---|
| 5,846,546 A | * | 12/1998 | Hurwitz et al. |
| 6,214,540 B1 | * | 4/2001 | DeVico et al. |
| 6,297,048 B1 | * | 10/2001 | Jolly et al. ............... 435/320.1 |
| 6,355,247 B1 | * | 3/2002 | Selby et al. |
| 6,383,774 B1 | * | 5/2002 | Chandrashekar |
| 6,569,418 B1 | * | 5/2003 | Garzino-Demo et al. .. 424/85.1 |

FOREIGN PATENT DOCUMENTS

| | | |
|---|---|---|
| WO | WO 94/28916 | 12/1994 |
| WO | WO 96/11279 | 4/1996 |
| WO | WO 96/36366 | 11/1996 |
| WO | WO 97/19696 | 6/1997 |
| WO | WO 98/15286 | 4/1998 |
| WO | WO 99/29728 | 6/1999 |

OTHER PUBLICATIONS

Nakano et al. Immunization with plasmid DNA encoding hepatitis C virus envelope E2 antigenic domains induces antibodies whose immune reactivity is linked to the injection mode pp. 7101–7109 vol. 71, No. 9.*

McCluskie et al. Route and method of delivery of DNA vaccine influence immune responses in mice and non–human primates pp. 287–300 1999.*

Gunn et al. A B–cell–homing chemokine made in lymphoid follicles activities burkitt's lymphoma receptor–1 pp. 799–803 1998.*

Nakano et al., Immunization with Plasmid DNA Encoding Hepatitis C Virus . . . , Sep. 1997, Journal of Virology, vol. 71, No. 9, pp. 7101–7109.*

Inxhauspe et al., Immune Response Against Hepatistis C Virus Structural Proteins Following Genetic Immunisation, 1998, vol. 92, pp. 163–168.*

Lagging et al., Immune Responses to Plasmid DNA Encoding the Heptitis C Virus Core Protein, Sep. 1995, Journal of Virology, vol. 69, No. 9, pp. 5859–5863.*

Walther et al., Viral Vector for Gene Transfer, Aug. 2000, Drugs, vol. 60, No. 2, pp. 249–271.*

Breitburd et al., Human papillomavirus vaccines, 1999, Cancer Biology, vol. 9, pp. 431–445.*

Howard et al., Nucleic Acid Vaccine Against Hepatitis Virus, 1998, Modulation of the Immune Response to Vaccine Antigens, vol. 92, pp. 157–162.*

Moldoveanu et al., "Immune Responses Induced by Administration of Encapsidated Poliovirus Replicons which Express HIV–1 *gag* and Envelope Proteins" *Vaccine* 13(11) :1013–1022, 1995.

Dilloo et al., "Combined Chemokine and Cytokine Gene Transfer Enhances Antitumor Immunity" *Nature Medicine* 2(10) :1090–1095, Oct., 1996.

Khudyakov et al., "Linear B–Cell Epitopes of the NS3–NS4–NS5 Proteins of the Hepatitis C Virus as Modeled with Synthetic Peptides" *Virology* 206:666–672, 1995.

* cited by examiner

*Primary Examiner*—Q. Janice Li
(74) *Attorney, Agent, or Firm*—Dahna S. Pasternak; Michael J. Moran; Alisa A. Harbin

(57) ABSTRACT

The immune response to a DNA immunogen in a mammal can be enhanced by administration of a chemokine or a polynucleotide encoding the chemokine. This method can be used, for example, to immunize or vaccinate a mammal against an infectious disease or a tumor.

23 Claims, 5 Drawing Sheets

FIG. 1

| CHIRON # | SFBR# | SEX | Wt. kg |
|---|---|---|---|
| CX544 | 11117 | | |
| CX545 | 11281 | | |
| CX546 | 10832 | | |
| CX547 | 11272 | | |

AVERAGE = #DIV/01

| STATUS | DATE | TOTAL TIME(WKS) | IMM# | IMMUNOGEN | BLEEDING SCHEDULE BLEED# | CYCLE "TIME" | CHIRON CLOTTED BLOOD FOR SERUM (ml) | CHIRON HEPARINIZED BLOOD BY (ml) | CHIRON ???? OTHER | TOTAL PER TIME (ml) | % OF MAX BLEED VOL | PERIOD |
|---|---|---|---|---|---|---|---|---|---|---|---|---|
| | NA | | - | - | - | - | | | | | | 13 |
| | NA | | - | - | - | - | 0 | 0 | | 0 | 0 | 0 |
| | NA | | - | - | - | - | 0 | 0 | | 0 | 0 | 0 |
| NEW | 9/23/97 | -2.0 | - | - | prebld 0 | - | 0 | 0 | | 0 | #DIV/01 | 0 |
| | 10/7/97 | 0.0 | 1 | pCMVKmANS | | 0.0 | 0 | 20 | | * 20 | | 1 |
| | 11/4/97 | 4.0 | 2 | pCMVKmANS | | 4.0 | 0 | 0 | | 0 | | 1 |
| | 11/18/97 | 6.0 | | | 1 | 8.0 | 0 | 0 | | 0 | | 1 |
| | 12/18/97 | 10.0 | | | 2 | 10.0 | 0 | 20 | | * 20 | #DIV/01 | 1 |
| | 1/8/98 | 13.0 | 3 | pCMVKmANS | | #REFI | 0 | 0 | | 0 | | 2 |
| | 1/20/98 | 16.0 | | | 3 | #REFI | 0 | 20 | | * 20 | | 2 |
| | 2/17/98 | 19.0 | | | 4 | #REFI | 0 | 20 | | * 20 | | 2 |
| | 3/17/98 | 23.0 | | | 5 | #REFI | 0 | 20 | | * 20 | #DIV/01 | 2 |
| | 4/7/98 | 26.0 | 4 | pCMVKmANS | | #REFI | 0 | 0 | | 0 | | 3 |
| | 4/21/98 | 28.0 | | | 6 | #REFI | 0 | 20 | | * 20 | | 3 |
| | 5/19/98 | 32.0 | | | 7 | #REFI | 0 | 20 | | * 20 | | 3 |
| | 6/16/98 | 36.0 | | | 8 | #REFI | 0 | 20 | | * 20 | #DIV/01 | 3 |
| | TBD | TBD | | | | | 0 | | | 0 | | 999 |
| | TBD | TBD | | | | | 0 | | | 0 | | 999 |
| | TBD | TBD | | | | | 0 | | | 0 | | 999 |

FIG. 2

| CHIRON # | SFBR # | SEX | Wt. kg |
|---|---|---|---|
| CX548 | 11538 | | |
| CX549 | 8854 | | |
| CX550 | 9421 | | |
| CX551 | 10645 | | |
| AVERAGE= | #DIV/0! | | |

| STATUS | DATE | TOTAL TIME(WKS) | IMM # | IMMUNOGEN | BLEEDING SCHEDULE BLEED # | CYCLE "TIME" | CHIRON CLOTTED BLOOD FOR SERUM (ml) | CHIRON HEPARINIZED BLOOD BY (ml) | CHIRON ???? OTHER | TOTAL PER TIME (ml) | % OF MAX BLEED VOL | PERIOD |
|---|---|---|---|---|---|---|---|---|---|---|---|---|
| | NA | | - | - | | | 0 | 0 | | 0 | | 13 |
| | NA | | - | - | | | 0 | 0 | | 0 | | 0 |
| | NA | | - | - | | | 0 | 0 | | 0 | | 0 |
| NEW | 9/25/97 | -2.0 | - | - | prebld 0 | - | 0 | 20 | | 0 | #DIV/0! | 0 |
| | 10/9/97 | 0.0 | 1 | NS-GM2 | | 0.0 | 0 | 0 | | 20 | | 1 |
| | 11/6/97 | 4.0 | 2 | NS-GM2 | | 4.0 | 0 | 0 | | 0 | | 1 |
| | 11/20/97 | 6.0 | | | 1 | 8.0 | 0 | 20 | | 0 | | 1 |
| | 12/18/97 | 10.0 | | | 2 | 10.0 | 0 | 20 | | 20 | #DIV/0! | 1 |
| | 1/8/98 | 13.0 | 3 | NS-GM2 | 3 | #REF! | 0 | 0 | | 0 | | 2 |
| | 1/22/98 | 16.0 | | | 4 | #REF! | 0 | 20 | | 20 | | 2 |
| | 2/19/98 | 19.0 | | | 5 | #REF! | 0 | 20 | | 20 | | 2 |
| | 3/19/98 | 23.0 | | | | #REF! | 0 | 20 | | 20 | #DIV/0! | 2 |
| | 4/9/98 | 26.0 | 4 | NS-GM2 | 6 | | 0 | 0 | | 0 | | 3 |
| | 4/23/98 | 28.0 | | | 7 | | 0 | 20 | | 20 | | 3 |
| | 5/21/98 | 32.0 | | | 8 | | 0 | 20 | | 20 | | 3 |
| | 6/18/98 | 38.0 | | | | | 0 | 20 | | 20 | #DIV/0! | 3 |
| | TBD | TBD | | | | | 0 | 0 | | 0 | | 999 |
| | TBD | TBD | | | | | 0 | 0 | | 0 | | 999 |
| | TBD | TBD | | | | | 0 | 0 | | 0 | | 999 |

FIG. 3

| CHIRON # | SFBR# | SEX | Wt. kg |
|---|---|---|---|
| CX552 | 9047 | | |
| CX553 | 9801 | | |
| CX554 | 10593 | | |
| CX555 | 10399 | | |
| | | AVERAGE= | #DIV/0! |

| STATUS | DATE | TOTAL TIME(WKS) | IMM# | IMMUNOGEN | BLEEDING SCHEDULE BLEED# | CYCLE "TIME" | CHIRON CLOTTED BLOOD FOR SERUM (ml) | CHIRON HEPA-RINIZED BLOOD BY (ml) | CHIRON ???? OTHER | TOTAL PER TIME (ml) | % OF MAX BLEED VOL | PERIOD |
|---|---|---|---|---|---|---|---|---|---|---|---|---|
| | NA | | - | - | | - | 0 | 0 | | 0 | | 13 |
| | NA | | - | - | | - | 0 | 0 | | 0 | | 0 |
| | NA | | - | - | | - | 0 | 0 | | 0 | #DIV/0! | 0 |
| NEW | 10/7/97 | -2.0 | - | - | prebld 0 | - | 0 | 20 | | * 20 | | 1 |
| | 10/21/97 | 0.0 | 1 | pCMVKmANS+pCMVLhRanise | | 0.0 | 0 | 0 | | 0 | | 1 |
| | 11/18/97 | 4.0 | 2 | pCMVKmANS+pCMVLhRanise | | 4.0 | 0 | 0 | | 0 | | 1 |
| | 12/2/97 | 6.0 | | | 1 | 8.0 | 0 | 20 | | * 20 | | 1 |
| | 12/30/97 | 10.0 | | | 2 | 10.0 | 0 | 20 | | * 20 | #DIV/0! | 1 |
| | 1/20/98 | 13.0 | 3 | pCMVKmANS+pCMVLhRanise | | #REF! | 0 | 0 | | 0 | | 2 |
| | 2/3/98 | 16.0 | | | 3 | #REF! | 0 | 20 | | * 20 | | 2 |
| | 3/3/98 | 19.0 | | | 4 | #REF! | 0 | 20 | | * 20 | | 2 |
| | 3/31/98 | 23.0 | | | 5 | #REF! | 0 | 20 | | * 20 | #DIV/0! | 2 |
| | 4/21/98 | 26.0 | 4 | pCMVKmANS+pCMVLhRanise | | #REF! | 0 | 0 | | 0 | | 3 |
| | 5/5/98 | 28.0 | | | 6 | #REF! | 0 | 20 | | * 20 | | 3 |
| | 6/2/98 | 32.0 | | | 7 | | 0 | 20 | | * 20 | | 3 |
| | 6/30/98 | 36.0 | | | 8 | | 0 | 20 | | * 20 | #DIV/0! | 3 |
| | TBD | | | | | | 0 | | | 0 | | 999 |
| | TBD | | | | | | 0 | | | 0 | | 999 |
| | TBD | | | | | | 0 | | | 0 | | 999 |

FIG. 4

| CHIRON # | SFBR# | SEX | Wt. kg |
|---|---|---|---|
| CX556 | 10850 | | |
| CX557 | 9009 | | |
| CX558 | 7750 | | |
| CX559 | 10242 | | |
| | AVERAGE= | | #DIV/01 |

| STATUS | DATE | TOTAL TIME(WKS) | IMM# | IMMUNOGEN | BLEEDING SCHEDULE BLEED# | BLEEDING SCHEDULE CYCLE "TIME" | CHIRON CLOTTED BLOOD FOR SERUM (ml) | CHIRON HEPARINIZED BLOOD BY (ml) | CHIRON ???? OTHER | TOTAL PER TIME (ml) | % OF MAX BLEED VOL | PERIOD 13 |
|---|---|---|---|---|---|---|---|---|---|---|---|---|
| | NA | | - | - | | | 0 | 0 | | 0 | 0 | 0 |
| | NA | | - | - | | | 0 | 0 | | 0 | 0 | 0 |
| | NA | | - | - | | | 0 | 0 | | 0 | #DIV/01 | 0 |
| NEW | 10/9/97 | -2.0 | | | prebld 0 | - | 0 | 0 | | 0 | 20 | 1 |
| | 10/23/97 | 0.0 | 1 | pCMVkmANS+pCMVLhMIP1a | | 0.0 | 0 | 0 | | * 0 | 20 | 1 |
| | 11/20/97 | 4.0 | 2 | pCMVkmANS+pCMVLhMIP1a | | 4.0 | 0 | 20 | | * 0 | 20 | 1 |
| | 12/4/97 | 6.0 | | | 1 | 6.0 | 0 | 0 | | 20 | #DIV/01 | 1 |
| | 1/1/98 | 10.0 | | | 2 | 10.0 | 0 | 0 | | 20 | #DIV/01 | 2 |
| | 1/22/98 | 13.0 | 3 | pCMVkmANS+pCMVLhMIP1a | | #REF! | 0 | 20 | | * 0 | 20 | 2 |
| | 2/5/98 | 16.0 | | | 3 | #REF! | 0 | 20 | | * 20 | #DIV/01 | 2 |
| | 3/5/98 | 19.0 | | | 4 | #REF! | 0 | 20 | | * 20 | #DIV/01 | 2 |
| | 4/2/98 | 23.0 | | | 5 | #REF! | 0 | 20 | | * 20 | #DIV/01 | 3 |
| | 4/23/98 | 26.0 | 4 | pCMVkmANS+pCMVLhMIP1a | | #REF! | 0 | 0 | | * 0 | 20 | 3 |
| | 5/7/98 | 28.0 | | | 6 | #REF! | 0 | 20 | | * 20 | #DIV/01 | 3 |
| | 6/4/98 | 32.0 | | | 7 | #REF! | 0 | 20 | | * 20 | #DIV/01 | 3 |
| | 7/2/98 | 38.0 | | | 8 | #REF! | 0 | 20 | | * 20 | #DIV/01 | 3 |
| | TBD | TBD | | | | | 0 | | | 0 | | 999 |
| | TBD | TBD | | | | | 0 | | | 0 | | 999 |
| | TBD | TBD | | | | | 0 | | | 0 | | 999 |

ENHANCING IMMUNE RESPONSES TO GENETIC IMMUNIZATION BY USING A CHEMOKINE

TECHNICAL AREA OF THE INVENTION

The invention relates to the area of immune responses to genetic immunization. More particularly, the invention relates to enhancing immune responses to DNA immunogens using immune co-stimulatory molecules.

BACKGROUND OF THE INVENTION

The use of genetic immunization, or immunization with DNA encoding polypeptide immunogens, to prime immune responses is viewed as a promising vaccine strategy. This technology offers potential improvements compared to other types of vaccines, such as subunit proteins complexed with adjuvants or inactivated or attenuated viral preparations. In addition to the practical advantages of simplicity of construction and modification, injection of genetic material encoding for polypeptide immunogens results in synthesis of the immunogens in the host. Thus, these immunogens are presented to the host immune system with native post-translational modifications, structure, and conformation.

In mice, several DNA vaccines have been effective at inducing long-lived antibody and cytotoxic T lymphocyte (CTL) responses and have conferred protective immunity against a number of viruses, bacteria, parasites, and tumors (1–8). Various approaches to enhance immune responses mediated by genetic immunization have been investigated. In addition to variations in dosage, route or boosting regimens, these variations include co-injection of polynucleotides encoding co-stimulatory molecules which improve immunogen presentation to lymphocytes, such as B7-1 or B7-2, or cytokines, such as GM-CSF, IL-2, IL-2, and IL-12, to create an optimal cytokine microenvironment for T cell priming (11–19). However, further enhancement of immune responses to genetic immunization is desirable for immunizing mammals, particularly humans, against immunogens such as virus- and tumor-specific immunogens.

Thus, there is a need in the art for methods of enhancing the immune responses to DNA immunogens.

SUMMARY OF THE INVENTION

It is an object of the invention to provide a method of enhancing an immune response to a DNA immunogen. This and other objects of the invention are provided by one or more of the embodiments described below.

One embodiment of the invention provides an immunogenic composition. The composition comprises a DNA immunogen and a chemokine or a polynucleotide encoding a chemokine.

Another embodiment of the invention provides a method of enhancing an immune response to a DNA immunogen in a mammal. A chemokine or a first polynucleotide encoding a chemokine and a DNA immunogen are administered to the mammal. An immune response to the DNA immunogen is thereby enhanced.

The present invention thus provides the art with the information that chemokines can be used to enhance an immune response of a mammal to a DNA immunogen. The invention can be used to, inter alia, to immunize or vaccinate a mammal against an infectious disease or a tumor.

BRIEF DESCRIPTION OF THE DRAWINGS

FIG. 1. FIG. 1 shows the immunization and bleeding schedules for animals immunized with HCV immunogens.

FIG. 2. FIG. 2 shows the immunization and bleeding schedules for animals immunized with granulocyte-macrophage colony-stimulating factor (GM-CSF).

FIG. 3. FIG. 3 shows the immunization and bleeding schedules for animals immunized with HCV immunogens and RANTES.

FIG. 4. FIG. 4 shows the immunization and bleeding schedules for animals immunized with HCV immunogens and macrophage inflammatory protein 1α(MIP-1α).

FIG. 5 shows the increased anti-HV gag antibody titer in mice immunized with a plasmid encoding HIV gag and a plasmid encoding the chemokine B lymphocyte chemokine (BLC).

DETAILED DESCRIPTION OF THE PREFERRED EMBODIMENTS

Figure 5:
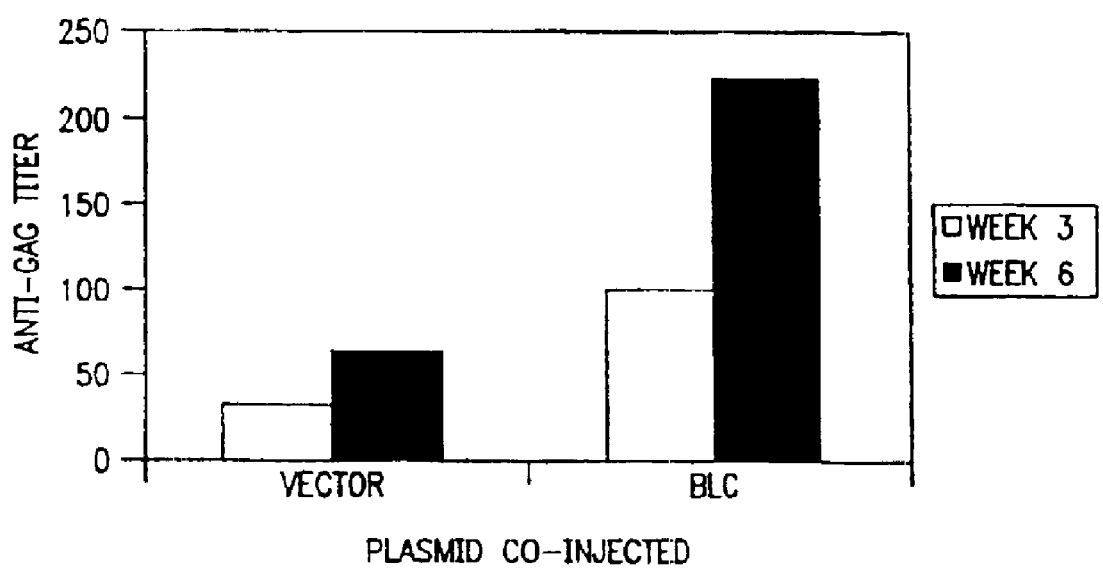
FIG. 5.

It is a discovery of the present invention that administration of a chemokine or a polynucleotide encoding a chemokine can be used to enhance an immune response a mammal to a DNA immunogen. This method can be used, inter alia, to increase immunological resistance to pathogens, such as viruses and bacteria, and to tumor-associated immunogens.

Chemokines generally function as chemoattractants for cells which they recruit from the blood to sites of infection. Thus, administration of a chemokine, either together with or in addition to a DNA immunogen, effectively recruits various cell populations, including antigen presenting cells and effector cells, to the site of administration or its vicinity. Similarly, administration of a polynucleotide encoding a chemokine can result in local chemokine secretion which induces migration of antigen presenting cells and/or lymphocytes to the site of administration and which enhances immune responses to the DNA immunogen. Local chemokine secretion can also enhance the migration of cells which have taken up the DNA immunogen or polypeptide encoded by the DNA immunogen to the lymph nodes, where priming of specific T cells occur.

Chemokines which can be used in the method of the invention include, but are not limited to, B lymphocyte chemokine (BLC), IL-8, PBP/β-TG/NAP-2, macrophage inflammatory proteins MIP-1α, MIP-1β, and MIP-3α, macrophage chemoattractant and activating factor (MCP-1 or MCAF), MCP-2, MCP-3, I-309, C10, HCC-1, RANTES (regulated upon activation, normal T cell expressed and secreted), lymphotactin, SCM-1, eotaxin, MGSA, PF4, NAP-2, IP-10, ENA-78, EMF-1, GCP-2, SLC, ELC, and SDF-1. Certain chemokines may be more effective in combination with a particular DNA immunogen than others at stimulating an immune response; optimization of the DNA immunogen-chemokine combination can be carried out using routine assays in standard animal models (see Examples 1 and 2).

The immune response which is enhanced can be any response which is influenced by chemnokines, including, but not limited to, antibody production or cytotoxic T lymphocyte (CTL) response resulting from chemoattraction and/or activation of antigen presenting cells, such as dendritic cells, macrophages, and monocytes, chemoattraction and/or activation of neutrophils, including eosinophils, and chemoattraction and/or activation of naive T cells, memory T cells, and pre-T cells to the thymus.

Measurement of enhanced immune responses can be carried out as is known in the art. For example, antibody titer can be measured by assays such as agglutination, immunoprecipitation, or ELISA.

Assays for chemotaxis relating to neutrophils are described in Walz et al. (1987), *Biochem Biophys. Res.*

Commun. 149: 755; Yoshimura et al. (1987), *Proc. Natl. Acad. Sci. USA* 84: 9233, and Schroder et al. (1987), *J. Immunol.* 139: 3474. Chemotaxis of lymphocytes can be assayed as described in Larsen et al., *Science* 243: 1464: (1989) and Carr et al., *Proc. Natl. Acad. Sci. USA* 91: 3652 (1994).

Assays for chemotaxis of tumor-infiltrating lymphocytes are descibed in Liao et al. (1995), *J. Exp. Med.* 182: 1301; for hemopoietic progenitors, in Aiuti et al. (1997), *J. Exp. Med.* 185: 111; for monocytes, in Valente et al. (1988), *Biochem.* 27: 4162; and for natural killer cells, in Loetscher et al. (1996), *J. Immunol.* 156: 322, and in Allavena et al. (1994), *Eur. J. Immunol.* 24: 3233.

Attraction or activation of eosinophils, dendritic cells, basophils, and neutrophils, can also be measured. Assays for determining eosinophil attraction are described in Dahinden et al., *J. Exp. Med.* 179: 751 (1994), Weber et al., *J. Immunol.* 154: 4166 (1995), and Noso et al., *Biochem. Biophys. Res. Commum* 200: 1470 (1994). Attraction of dendritic cells can be measured as described, for example, in Sozzani et al., *J. Immunol.* 155: 3292 (1995). Assays for attracting basophils are taught in Dahinden et al., *J. Exp. Med.* 179: 751 (1994), Alam et al., *J. Immunol.* 152: 1298 (1994), and Alam et al., *J. Exp. Med.* 176: 781 (1992). Activation of neutrophils is taught in Maghazaci et al., *Eur. J. Immunol.* 26: 315 (1996) and Taub et al., *J. Immunol.* 155: 3877 (1995). Cytotoxic T lymphocyte assays can also be used to measure enhanced immune response to a DNA immunogen (see Example 1, below).

The DNA immunogen can be any contiguous sequence of deoxyribonucleotides encoding a polypeptide which is capable of eliciting an immune response. For example, polynucleotides encoding immunogenic polypeptides of viruses such as HIV viruses (e.g, gag, pol, or env), herpes viruses (i.e., HSV-1, HSV-2), Epstein-Barr virus, varicela-zoster virus, cytomegalovirus, and hepatitis B virus (HBV), hepatitis C virus (HCV), and human papilloma viruses (i.e., HPV-16,-18, and -31) can serve as a DNA immunogen. DNA which encodes polypeptide immunogens of other infectious agents, such as bacteria, fungi, or yeast, can function as a DNA immunogen in the method of the invention. DNA which encodes polypeptides specifically expressed by a tumor, such as EGFRvIII, Ras, or p185$^{HER2}$, or polypeptides which are expressed both by a tumor and by the corresponding normal tissue, can also function as a DNA immunogen. If desired, a DNA immunogen can comprise coding sequences for more than one immunogenic polypeptide.

A chemokine and a DNA immunogen can be administered to a mammal, preferably a human, by any means known in the art, including parenteral, intranasal, or intramuscular injection, or coated onto small metal projectiles and injected using a biological ballistic gun ("gene gun"). Alternatively, a chemnokine and a DNA immunogen can be administered successively. The chemokine can be administered prior to administration of the DNA immunogen, or the DNA immunogen can be administered prior to the administration of the chemokine.

A polynucleotide encoding the chemokine can also be administered. Preferably, a polynucleotide encoding the chemokine and a polynucleotide comprising the DNA immunogen are co-injected. The polynucleotides can also be administered successively, in any order. For co-administration, a single polynucleotide comprising both chemokine-encoding sequences and the DNA immunogen can be administered, or the DNA immunogen and the chemokine-encoding polynucleotide can be provided separately and mixed together prior to administration.

The invention also provides immunogenic compositions comprising a DNA immunogen and a chemokine or a polynucleotide encoding a chemokine. The composition can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymer, and inactive virus particles. Pharmaceutically acceptable salts can also be used in compositions of the invention, for example, mineral salts such as hydrochlorides, hydrobromides, phosphates, or sulfates, as well of organic acids such as acetates, proprionates, malonates, or benzoates. Compositions of the invention can also contain liquids, such as water, saline, glycerol, and ethanol, as well as substances such as wetting agents, emulsifying agents, or pH buffering agents. Liposomes, such as those described in U.S. Pat. No. 5,422, 120, WO 95/113796, WO 91/14445, or EP 524,968 B1, can also be used as a carrier for a composition of the invention.

Compositions of the invention can be used as vaccine compositions, for example, to enhance an immune response of a mammal, including a human, to an infectious agent or a tumor. The particular dosages of chemokine and DNA immunogen which are sufficient to enhance an immune response to the DNA immunogen will vary according to the chemokine and DNA immunogen being used and the mammal to which the chemokine and DNA immunogen are being administered. The amounts of each active agent in the examples described below provide general guidance for the range of each component to be utilized by the practitioner upon optimizing the method of the present invention for practice either in vitro or in vivo. Generally, 0.1, 0.2, 0.3, 0.4, 0.5, 0.75, 1.0, 1.5, 2.0, 2.5, or 5 mg of a chemokine protein, a polynucleotide encoding a chemokine, or a polynucleotide comprising a DNA immunogen will be administered to a large mammal, such as a baboon or a human.

Such ranges by no means preclude use of a higher or lower amount of a component, as might be warranted in a particular application. For example, the actual dose and schedule may vary depending on whether the compositions are administered in combination with other pharmaceutical compositions or depending on individual differences in pharmacokinetics, drug disposition, and metabolism.

The following are provided for exemplification purposes only and are not intended to limit the scope of the invention described in broad terms above.

EXAMPLE 1

Co-administration of HCV immunogens and MIP-1 αincreases lysis of autologous B cells infected with vaccinia virus encoding HCV polypeptide NS3

HCV immunogens. Each plasmid comprises a CMV enhancer/promoter and is Kanamycin-resistant. Plasmids were prepared by an alkaline lysis method from *E. coli* bacteria and purified using Qiagen purification systems. After purification, plasmids were stored at −80° C., at a concentration of 1 mg/ml.

Plasmid pCMVKΔNS comprises hepatitis C viral DNA encoding HCV polypeptides ΔNS3, NS4, NS5a, and NS5b (immunogen for animal Group 1). Plasmid NS-GM2 encodes HCV polypeptides ΔNS3, NS4, NS5b, NS5b, and hGM-CSF (immunogen for animal Group 2). Plasmid pCMVLhRantes encodes human RANTES protein, pCMVLhMIP-1Δ encodes MIP-1Δ.

For the immunization protocols described below, pCMVKmΔNS was premixed with either pCMVLhRantes (immunogen for animal Group 3) or pCMVLhMIP1Δ (immunogen for animal Group 4). Each plasmid was at a concentration of 1 mg/ml of DNA, for a total of 2 mg/ml of DNA per mixed immunogen.

Injection of HCV immunogens into baboons. On the day of injection, one vial (marked with the plasmid name and animal group) per animal was removed from the freezer, thawed at room temperature, and gently mixed. Each immunogen was injected both intramuscularly and intradermally. The total volume injected per animal was 1 ml.

The left and right tibialis anterior muscle was injected with 400 μl of DNA for a total of 800 μl intramuscular injection per baboon, using a 1 ml syringe. The immunogens were injected slowly, over about 10 seconds. After injection, the needle was removed slowly, to reduce leakage.

Each of two separates sites of the upper back was injected with 100 μl of DNA for a total of 200 μl intradermal injection per baboon, using a 0.3 ml U-100 Insulin syringe. The skin at the sites of injection was shaved. At each site, the needle was inserted the needle bevel up into the skin and then rotated 90 degrees so that the bevel pointed to the side. The 100 μl was slowly injected over about 10 seconds. After injection, the needle was slowly rotated so that the bevel was up again, then withdrawn slowly to reduce leakage.

Immunization and bleeding schedules for four groups of baboons. Baboons in each of four groups were immunized and bled according to the following schedule. Group 1 (animals CK544, CK545, CK546, and CK547) received inoculations of pCMVKmΔNS (HCV immunogens) and were bled according to the schedule in FIG. 1. Group 2 (animals CK548, CK549, CK550, and CK551) received inoculations of NS-GM2 (HCV immunogens and GM-CSF) and were bled according to the schedule in FIG. 2. Group 3 (animals CK552, CK553, CK554, and CK555) received inoculations of pCMVKmΔNS and pCMVLhRantes (HCV immunogens and RANTES) according to the schedule in FIG. 3. Group 4 (animals CK556, CK557, CK558, and CK559) received inoculations of pCMVKmΔNS and pCMVLhMIP1a (HCV immunogens and MIP-1Δ) and were bled according to the schedule in FIG. 4.

Immunizations were carried out as described in Example 2, above. At each of the times indicated in the bleeding schedules, blood was drawn from the femoral vein while the baboons were under anesthesia (Ketamine®, 10 mg/ml). Blood was treated with heparin. B and T cells were isolated from these blood samples and used in the cytotoxic T lymphocyte assays described below.

CTL assays. Autologous B cell lines from each animal were established by transforming B cells with *H. papio*. Separate samples of peripheral blood mononuclear cells were restimulated with immortalized autologous B cells infected with a recombinant vaccinia virus that encodes each of the HCV immunogens (NS3, NS4, NS5a, and NS5b). Two weeks later, CD8+ T lymphocytes were purified from the samples using magnetic beads.

The ability of T cells from each animal to lyse its autologous B cell line infected with vaccinia virus encoding the same immunogens used to immunize the animals was tested using a standard $^{51}$Cr-release assay. Ratios of effector (T cells) to-target (B cells) of 40:1, 10:1, and 2:1 were tested.

Percent lysis was calculated in each assay. A positive CTL response was noted if at least 10% more lysis occurred with homologous cells (stimulated with a vaccinia virus encoding an HCV immunogen) than with heterologous cells (stimulated with a vaccinia virus encoding an unrelated immunogen) for each of the two highest effector to target cell ratios tested.

Table I shows the number of animals with positive responses in a cytotoxic T lymphocyte assay.

TABLE I

| Number of animals with CTL responses | |
|---|---|
| Immunogen | No. of Animals |
| pCMVNS3-5 | 0/4 |
| pCMVNS3-5 & MIP-1α | 1/4 |
| pCMVNS3-5 & RANTES | 0/4 |

Table II shows percent lysis of target cells from animal CK556 after restimulation. Homologous cells were stimulated with vaccinia virus encoding HCV polypeptide NS3.

TABLE II

| Percent lysis of targets after restimulation (animal CK556) | | | |
|---|---|---|---|
| | Effector:Target | Homologous[1] | Heterologous[2] |
| pre-immunization | 40:1 | 2 | 11 |
| pre-immunization | 10:1 | 6 | 10 |
| pre-immunization | 2:1 | 7 | 6 |
| 2 weeks post 3rd immunization | 40:1 | 27 | <1 |
| 2 weeks post 3rd immunization | 10:1 | 17 | <1 |
| 2 weeks post 3rd immunization | 2:1 | 11 | <1 |

[1]stimulated with a vaccinia encoding HCV polypeptide NS3.
[2]stimulated with a vaccinia encoding an unrelated immunogen.

The results reported in Table II demonstrate that co-administration of HCV immunogens and the chemokine MIP-1 α resulted in an increased lysis of autologous B cells infected with vaccinia virus encoding HCV polypeptide NS3.

EXAMPLE 2

Co-administration of HIV immunogens and BLC increases the titer of anti-p55gag

Balb/c mice received bilateral injections into the anterior tibialis muscle of 10 μg of a plasmid, which encodes HIV gag, either alone or together with a total of 100 μg of a plasmid encoding B lymphocyte chemokine (BLC; *Nature* 391, 799–803, 1998). Fifty μg of BLC-encoding plasmid were injected into each muscle.

The animals were bled at 3 and 6 weeks after immunization, and anti-p55gag antibody titer was measured by ELISA. FIG. 5 shows that anti-gag antibody titer in immunized mice is increased at three weeks after immunization and continues to increase up to at least six weeks.

Numbered References

1. Ulmer, J., et al. 1993. Heterologous protection against influenze by injection of DNA encoding a viral protein [see comments]. *Science* 259:1745–9.
2. Fynan, E., R. et al. 1993. DNA vaccines: protective immunizations by parenteral, mucosal, and gene-gun inoculations. *Proc Natl Acad Sci USA* 90:11478–82.
3. Cox, G., et al. 1993. Bovine herpesvirus 1: immune responses in mice and cattle injected with plasmid DNA. *J Virol* 67:5664–7.
4. Sedegah, M., et al. 1994. Protection against malaria by immunization with plasmid DNA encoding circumsporozoite protein. *Proc Natl Acad Sci USA* 91:9866–70.
5. Barry, M., et al. 1995. Protection against mycoplasma infection using expression-library immunization. *Nature* 377–632–5.
6. Conry, R., et al. 1995. A carcinoembryonic antigen polynucleotide vaccine has in vivo antitumor activity. *Gene Ther* 2:59–65.

7. Syrengelas, A., et al. 1996. DNA immunization induces protective immunity against B-cell lymphoma. *Nat Med* 2:1038–1041.

8. Tascon, R., et al. 1996. Vaccination against tuberculosis by DNA injection. *Nat Med* 2:888–92.

9. Yautomi, Y., et al. 1996. Simian immunodeficiency virus-specific cytotoxic T-lymphocyte induction through DNA vaccination of rhesus monkeys. *J Virol* 70:678–8 1.

10. Letvin, M., et al. 1997. Potent protective anti-HIV immune responses generated by bimodal HIV envelope DNA plus protein vaccination. *Proc Nat Acad Sci USA* 94:9378–9383.

11. Xiang, Z., and H. Ertl. 1995. Manipulation of the immune responses to a plasmid-encoded viral antigen by coinoculation with plasmids expressing cytokines. *Immunity* 2:129–35.

12. Conry, R., et al. 1996. Selected strategies to augment polynucleotide immunization. *Gene Ther* 3:67–74.

13. Irvine, K., et al. 1996. Cytokine enhancement of DNA immunization leads to effective treatment of established pulmonary metastases. *J. Immunol* 156:238–45.

14. Chow, Y., et al. 1997. Improvement of hepatitis B virus DNA vaccines by plasmids coexpressing hepatitis B Surface antigen and interleukin-2. *J Virol* 71:169–78.

15. Iwasaki, A., et al. 1997. Enhanced CTL responses mediated by plasmid DNA immunogens encoding costimulatory molecules and cytokines. *J Immmunol* 158:4591–601.

16. Kim, J., et al. 1997. In vivo engineering of a cellular immune response by coadmistration of IL-12 expression vector with a DNA immunogen. *J Immunol* 158:816–26.

17. Okada, E., et al. 1997. Intranasal immunization of a DNA vaccine with IL-12- and granulocyte-macrophage colony-stimulating factor (GM-CSF)-expressing plasmids in liposomes induces strong mucosal and cell-mediated immune responses against HIV-1 antigens. *J Immunol* 159:3638–47.

18. Geissler, M., et al. 1997. Enhancement of cellular and humoral immune responses to hepatitis C viruws core proteins using DNA-based vaccines augmented with cytokine-expressing plasmids. *J Immunol* 158:1231–7.

19. Larsen, D., et al. 1998. Coadministration of DNA encoding interleukin-6 and hemagglutinin confers protection from influenza virus challenge in mice. *J Virol* 72:1704–8.

20. Butcher, E. 1991. Leukocyte-endothelial cell recogtnition: three (or more) steps to specificity and diversity. *Cell* 67:1033–6.

21. Springer, T. 1994. Traffic signals for lymphocyte recirculation and leukocyte emigration: the multistep paradigm. *Cell* 76:301–14.

22. Butcher, E., and L. Picker. 1996. Lymphocyte homing and homeostasis. *Science* 272:60–6.

23. Schall, T., and K. Bacon. 1994. Chemokines, leukocyte trafficking, and inflammation. *Curr Opin Immunol* 6:865–73.

24. Taub, D., et al. 1993. Preferential migration of activated CD4+ and CD8+ T cells in response to MIP-1 alpha and MIP-1 beta *Science* 260:355–8.

25. Schall, T., et al. 1993. Human macrophage inflammatory protein alpha (MIP-1 alpha) and MIP-1 beta chemokines attract distinct populations of lymphocytes. *J Exp Med* 177:1821–6.

26. Schall, T., et al. 1990. Selective attraction of monocytes and T lymphocytes of the memory phenotype by cytokine RANTES. *Nature* 347:669–71.

27. Rot, A., et al. 1992. RANTES and macrophage inflammatory protein 1 alpha induce the migration and activation of normal human eosinophil granulocytes. *J Exp Med* 176:1489–95.

I claim:

1. An immunogenic composition comprising:
   a plasmid comprising a sequence encoding an immunogen; and
   a B lymphocyte chemoattractant (BLC) or a polynucleotide encoding a B lymphocyte chemoattractant (BLC).

2. The immunogenic composition of claim 1 wherein the immunogen is a viral immunogen.

3. The immunogenic composition of claim 2 wherein the viral immunogen is a hepatitis C virus non-structural polypeptide.

4. The immunogenic composition of claim 3 wherein the hepatitis C virus non-structural polypeptide is selected from the group consisting of NS3, NS4, NS5a, and NS5b.

5. The immunogenic composition of claim 2 wherein the viral immunogen is an HIV polypeptide.

6. The immunogenic composition of claim 5 wherein the HIV polypeptide is a gag polypeptide.

7. The immunogenic composition of claim 1 wherein the immunogen comprises a tumor immunogen.

8. The immunogenic composition of claim 1 further comprising a pharmaceutically acceptable carrier.

9. A method of enhancing an immune response to a viral immunogen in a mammal comprising the step of: intramuscularly or intradermally administering to the mammal (i) a B lymphocyte chemoattractant (BLC) or a polynucleotide encoding a B lymphocyte chemoattractant (BLC) and (ii) a plasmid comprising a single promoter derived from a virus operably linked to a sequence encoding a viral immunogen, whereby an immune response to the viral immunogen is enhanced.

10. The method of claim 9 wherein the first polynucleotide encoding the BLC is administered.

11. The method of claim 10 wherein the first polynucleotide and the plasmid are co-administered.

12. The method of claim 10 wherein the first polynucleotide is administered prior to administration of the plasmid.

13. The method of claim 10 wherein the plasmid is administered prior to administration of the first polynucleotide.

14. The method of claim 10 wherein a second polynucleotide is administered, the second polynucleotide comprising (a) the first polynucleotide and (b) a sequence encoding a viral immunogen.

15. The method of claim 9 wherein the viral immunogen is a hepatitis C virus non-structural polypeptide.

16. The method of claim 15 wherein the hepatitis C virus non-structural polypeptide is selected from the group consisting of NS3, NS4, NS5a, and NS5b.

17. The method of claim 9 wherein the viral immunogen is an HIV polypeptide.

18. The method of claim 17 wherein the HIV polypeptide is a gag polypeptide.

19. The method of claim 9 wherein the mammal is human.

20. The method of claim 9 wherein the immune response is an antibody response.

21. The method of claim 9 wherein the immune response is a cytotoxic T lymphocyte response.

22. A method of enhancing an immune response to a viral immunogen in a mammal comprising the step of:
   intramuscularly or intradermally administering to the mammal (i) a lymphocyte chemoattractant (BLC) or a polynucleotide encoding a B lymphocyte chemoattractant (BLC) and (ii) a plasmid comprising a sequence encoding a viral immunogen, wherein (i) and (ii) are administered successively in any order, and whereby an immune response to the viral immunogen is enhanced.

23. A method of eliciting an immune response to a viral immunogen in a mammal, the method consisting of the step of:

intramuscularly or intradermally administering to the mammal (i) a B lymphocyte chemoattractant (BLC) or a polynucleotide encoding a B lymphocyte chemoattractant (BLC) and (ii) a plasmid comprising a single promoter derived from a virus operably linked to a sequence encoding a viral immunogen, whereby an immune response to the viral immunogen is enhanced.

* * * * *

UNITED STATES PATENT AND TRADEMARK OFFICE
CERTIFICATE OF CORRECTION

PATENT NO. : 6,919,318 B1
DATED : July 19, 2005
INVENTOR(S) : Xavier Paliard

Page 1 of 1

It is certified that error appears in the above-identified patent and that said Letters Patent is hereby corrected as shown below:

Title page,
Item [60], Related U.S. Application Data, delete "PCT/US99/08802, filed on April 22, 1999" and insert in lieu thereof -- 60/082,600 filed on April 22, 1998 --.

Column 9,
Line 64, delete "a lymphocyte" and insert in lieu thereof -- a B lymphocyte --.

Signed and Sealed this

Twenty-seventh Day of September, 2005

JON W. DUDAS
*Director of the United States Patent and Trademark Office*